United States Patent [19]
Williams et al.

[11] Patent Number: 5,327,883
[45] Date of Patent: Jul. 12, 1994

[54] APPARATUS FOR AEROSOLIZING POWDERED MEDICINE AND PROCESS AND USING

[75] Inventors: David R. Williams, San Diego, Calif.; Mark B. Mecikalski, Tucson, Ariz.; David O. Thueson, Poway, Calif.

[73] Assignee: Dura Pharmaceuticals, Inc., San Diego, Calif.

[21] Appl. No.: 702,297

[22] Filed: May 20, 1991

[51] Int. Cl.$^5$ .......................................... A61M 15/00
[52] U.S. Cl. ........................ 128/203.12; 128/203.15; 128/203.21
[58] Field of Search ................... 128/203.12, 203.15, 128/203.21

[56] References Cited

U.S. PATENT DOCUMENTS

| | | | |
|---|---|---|---|
| 3,507,277 | 4/1970 | Altounyan et al. | 128/203.15 |
| 3,518,992 | 7/1970 | Altounyan et al. | 128/203.21 |
| 3,635,219 | 1/1972 | Altounyan et al. | 128/203.15 |
| 3,669,113 | 6/1972 | Altounyan et al. | 128/203.15 |
| 3,812,853 | 5/1974 | Crain | 128/200.17 |
| 3,831,606 | 8/1974 | Damani | 128/203.15 |
| 3,971,377 | 7/1976 | Damani | 128/203.21 |
| 4,147,166 | 4/1979 | Hansen | 128/203.15 |
| 4,307,734 | 12/1981 | Blankenship | 128/203.15 |
| 4,452,239 | 6/1984 | Malem | 128/200.14 |
| 4,509,515 | 4/1985 | Altounyan et al. | 128/200.23 |
| 4,524,769 | 6/1985 | Wetterlin | 128/203.15 |
| 4,534,343 | 8/1985 | Nowacki et al. | 128/203.15 |
| 4,627,432 | 12/1986 | Newell et al. | 128/203.21 |
| 4,668,218 | 5/1987 | Virtanen | 128/203.15 |
| 4,739,754 | 4/1988 | Shaner | 128/203.15 |
| 5,033,463 | 7/1991 | Cocozza | 128/203.15 |
| 5,113,855 | 5/1992 | Newhouse | 128/203.15 |
| 5,161,524 | 11/1992 | Evans | 128/203.15 |
| 5,176,132 | 1/1993 | Drought et al. | 128/203.15 |

FOREIGN PATENT DOCUMENTS

| | | |
|---|---|---|
| 1491715 | 12/1976 | Fed. Rep. of Germany . |
| 1262085 | 2/1972 | United Kingdom . |
| 2248400 | 4/1992 | United Kingdom . |

OTHER PUBLICATIONS

D. Ganderton et al., "Dry Powder Inhalers", Advances in Pharmaceutical Sciences, pp. 165–191.
Research Disclosure–"Improved Inhalation Device", 32187, p. 57.
N. A. Fuchs, The Mechanics of Aerosols, 1964, pp. 353–377.

Primary Examiner—Edgar S. Burr
Assistant Examiner—Aaron J. Lewis
Attorney, Agent, or Firm—Lyon & Lyon

[57] ABSTRACT

An apparatus for aerosolizing a dose of powdered medicine for inhalation, comprising in combination a solid core defining a diskshaped aerosolizing chamber, the chamber defined by spaced-apart, flat front and rear walls terminated by a circumferential wall, the core including a first end piece having formed therein a hollow mouth/nose piece at the front thereof, an impeller non-concentrically disposed in the chamber mounted on a shaft for high-speed powered rotation about a fixed axis, a plunger for instantaneously introducing a full dose of powdered medicine into the aerosolizing chamber so that all particles thereof are available for intermixing disaggregation and comminution, an aperture for receiving a first stream of air interior the core and passing it towards the mouthpiece for inhalation by the user, and, a wall having formed therein at least one aperture for diverting a portion of the first stream into a second stream of air for sweeping through the aerosolizing chamber to mix with the particles to form a fine, low-density, low-velocity, dry mist of powdered medicine for inhalation by the user.

22 Claims, 2 Drawing Sheets

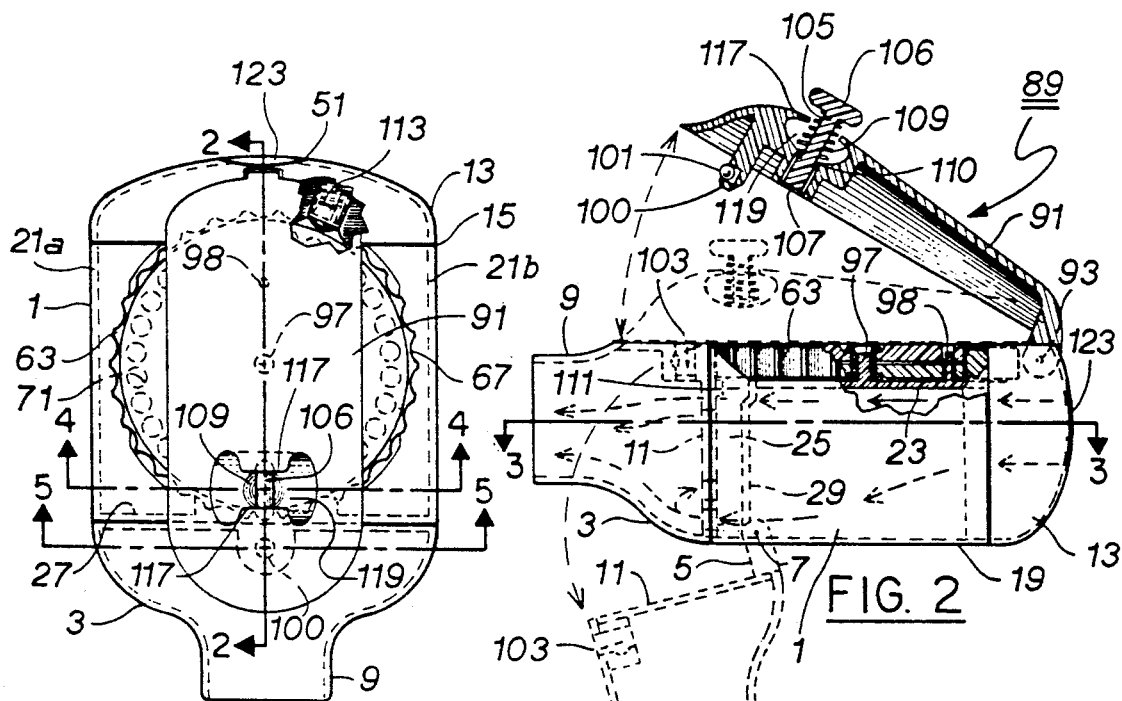
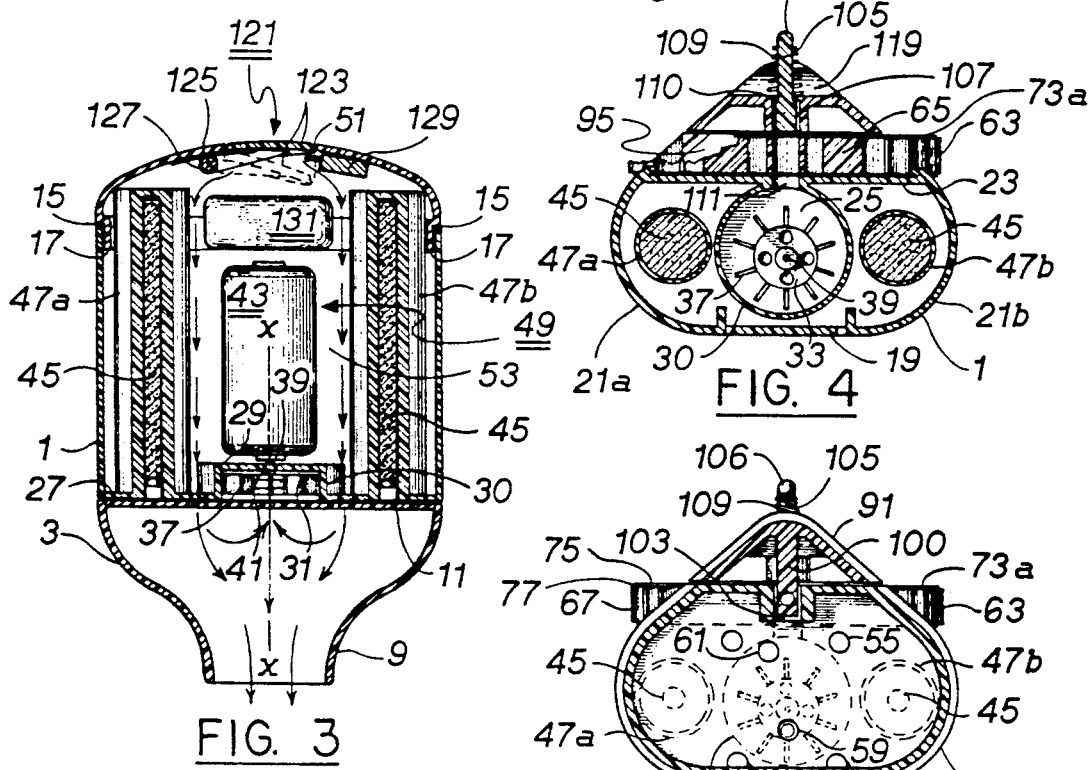
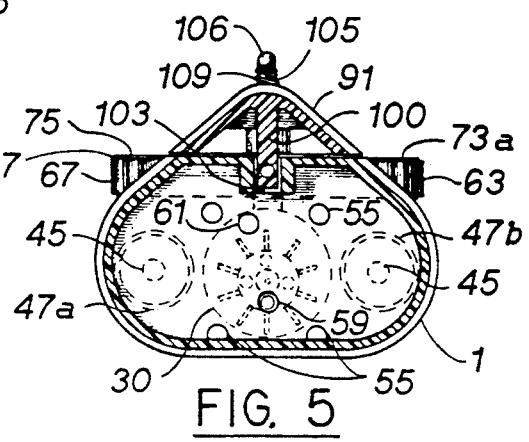

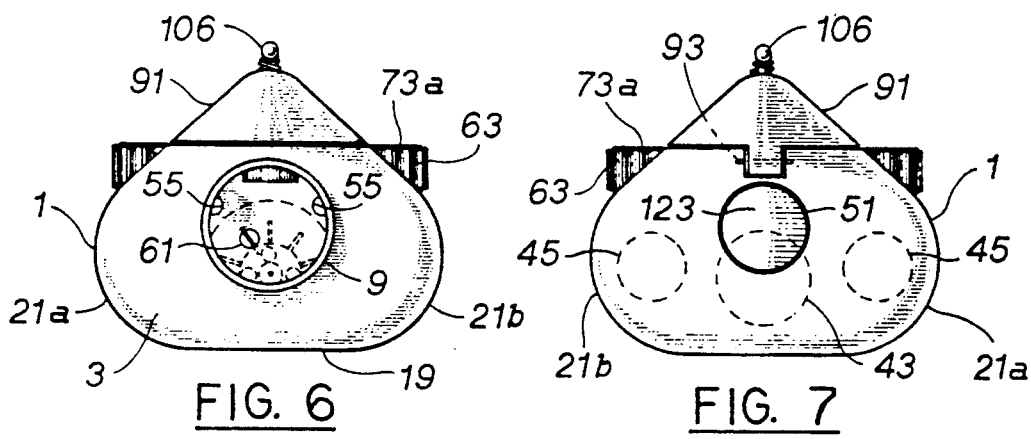
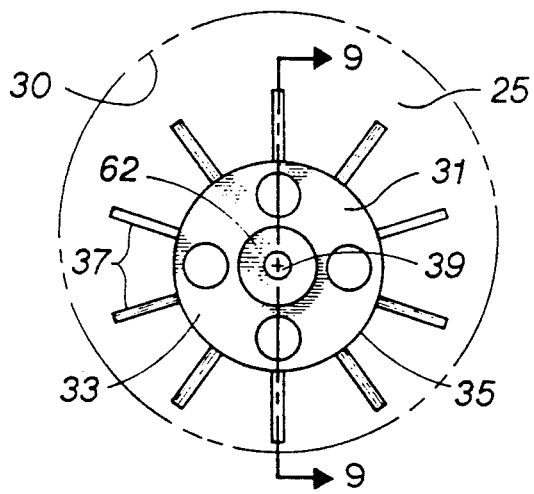
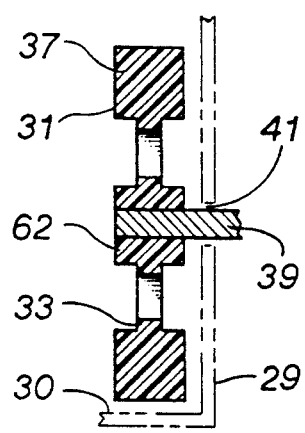
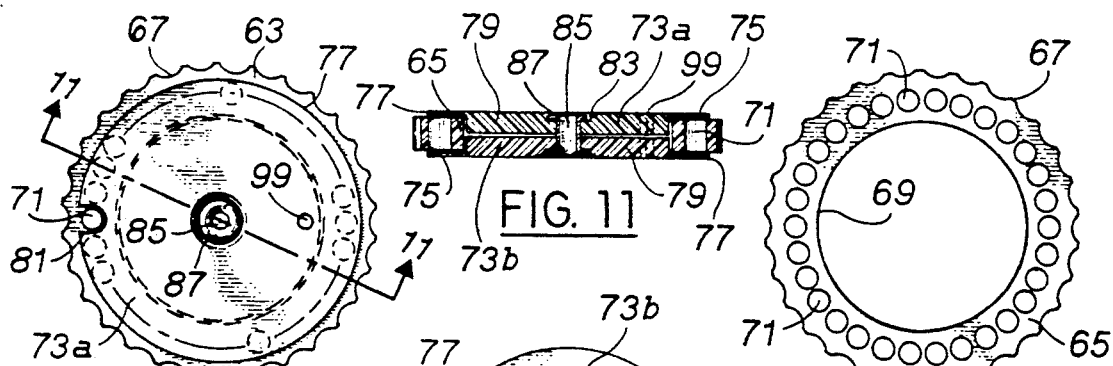
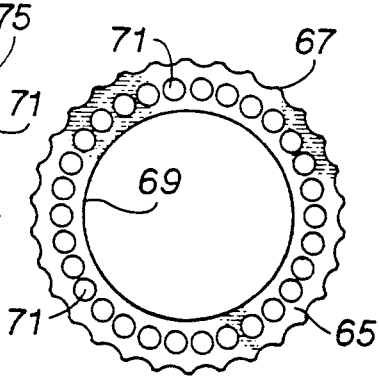
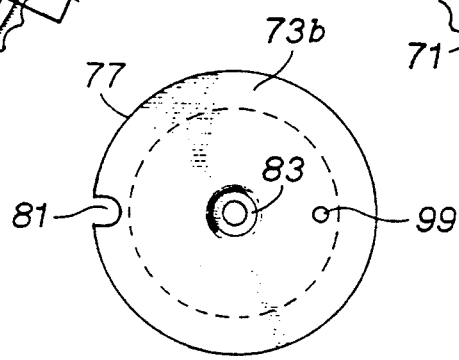

APPARATUS FOR AEROSOLIZING POWDERED MEDICINE AND PROCESS AND USING

BACKGROUND OF THE INVENTION

1. Field of the Invention

This invention pertains to the field of administering powdered medicines in aerosol form, directly to the lungs through the throat or nasal passages. More particularly, the invention relates to an apparatus for aerosolizing and delivering medicines to the user and of a process of preparing these medicines so that repeated, accurate doses may be administered using the apparatus.

2. Description of the Prior Art

Beginning in the early 1970's, it was found that certain medicines could be administered in dry-powder form directly to the lungs by inhalation through the mouth or inspiration through the nose. This process allows the medicine to bypass the digestive system, and in some cases, allows smaller doses to be used to achieve the same desired results as orally ingested medicines. In other cases, it provides an administrative technique for medicines that display unacceptable side effects when taken by other methods.

Various devices that form inhalable mists of medicines have been invented and exist in the prior art. They are divided between those that form mists of liquid medicines, those that form mists of powdered medicines, and those that may be used to form mists of both liquids and powders. The physical characteristics of powdered medicines, with their particle sizes ranging from about 1 to about 100 microns (one micron equals one-thousandth of a millimeter), and more commonly from about 1 to about 5 microns, are so different from that of liquid medicines, there is rarely any similarity between the engineering requirements and the physical constructions of the two types of devices.

Typical prior art devices for handling dry medicines are shown and described in U.S. Pat. Nos. 3,507,277; 3,518,992; 3,635,219; 3,831,606; 3,971,377; and 4,147,166. Many of these devices have been commercialized, however, most of them have not found wide acceptance. For instance, most of these prior art devices use powdered medicine contained in a gelatin capsule with a separate dose contained in each capsule. These capsules are small and require some degree of manual dexterity to load and unload. A large portion of potential users of dry powdered medicines are found in the senior-citizen sector of the population and, unfortunately, this coincides with the major group of those inflicted with various forms of arthritis. With the minute size of the capsules and the requirements to load and unload them each time the nebulizer is used, they are difficult for these people to use.

Further, loading individual capsules with individual doses of powdered medicines is time-consuming and thus makes the dosage in capsule form a costly item. People who use a nebulizer during their daily routine are required to carry a large number of capsules. This could lead to breakage of some capsules and loss of the medicine contained therein. In other situations, the capsule might leak thus lowering the effective dosage of the medicine.

From a mechanical point of view, virtually all of the devices involve the use of capsules containing the medicines that are pierced along their sides by needles or other sharp objects. Thereafter, the powdered medicine is slowly withdrawn from the capsules by either partial vacuum, caused by forced inspiration by the individual, or by centrifugal force. Some of these patents indicate the extraction process requires forced inspiration for as long as two and one-half minutes. This time period would require the user to repeatedly inhale rather large volumes of air, each with a little dose of the medicine, often resulting in dizziness. In addition, any time a powder is extracted through a slit in a flexible capsule wall there is a significant question as to whether or not all the powder is totally inhaled.

Water can pass through the walls of gelatin capsules. In high humidity areas, as when carried in one's pocket, such water vapor could penetrate the capsule and cake the medicine contained therein. If caked, it is extremely unlikely that all of the medicine would be inhaled from the capsule so that the dosage between capsules would vary thus reducing the effect of the medicine.

Slow introduction of powdered medicine from the perforated capsule into the aerosolizing chamber, coupled with the airflow through the chamber, means that not all of the powder particles are present in the chamber at any one time. It has been found that self-scouring and inter-particle contact is an important feature in aerosolizing the powdered medicine. It has also now been found that these small particles have a tendency to build up in the aerosolizing chamber.

Much discussion has been made in the prior art concerning whether or not to allow the user to exhale into the device. The perforated capsules admit medicine very slowly into the inhalating airstream. In addition, many users are elderly persons or those who suffer from lung disease. These two factors often combine to render the user incapable of inhaling all of the medicine in one breath. Therefore, it is important to deal with the possibility that the user will exhale into the device. Exhaling involves a high-humidity airstream and, when it enters the inhalating device, may cause some plating of moisture on the interior walls. In other cases, moisture-laden air is blown into the aerosolizing chamber causing the powdered medicine to cake and fail to be extracted by later inhalations. Notwithstanding the attempts in the prior art to limit the introduction of exhaled moisture-laden air into the aerosolizing chamber, the fact remains that repeated exhaling into the device will inject a noticeable amount of moisture into the unit, thus causing cake buildup and loss of dosage.

Further, in devices where outside air is directly introduced into the aerosolizing chamber, exhaling into the unit while medicine is still being extracted from the capsule will cause medicine to be blown out of the air intake apertures. Indeed, one of the prior-art patents describes a typical inhalation treatment as recovering only 50 percent of the medicine dose contained in the capsule. Accordingly, the best manner in dealing with the problem of exhaling into the device is to just prevent it altogether—something not readily accomplished by the prior art.

Finally, the prior art has apparently not fully appreciated the advantages of reducing the size of large particles or agglomerated particles during use of the device. Large or agglomerated particles of medicine being heavier gather momentum during forced inhalation and impact the soft, wet tissue at the back of the throat instead of remaining in the air flow for deposit in the lungs. When this occurs, much of the medicine does not reach deep into the interior of the lungs and thus is not placed in a strategic location where it will be solvated for direct absorption through the areolar tissue into the blood stream. In more severe cases, such impact causes uncontrollable coughing and thus forces large volumes of moisture-laden air, as well as finely dispersed saliva, to be reinjected into the device thus causing the caking problems heretofore described.

SUMMARY OF THE INVENTION

An improved apparatus for aerosolizing repeated doses of dry powdered medication is portable and small enough to be easily carried on one's person for use whenever needed. Instead of a single-dose gelatin capsule of medicine, a multi-dose cartridge is used, said cartridge carrying a plurality of doses, each ready for use by merely turning the cartridge to a new position. Instead of dribbling the medicine into the device, each dose of medicine is fully and instantaneously injected into the aerosolizing chamber through mechanical means to allow all of the powdered medicine to be present at one time, and to allow it to undergo self-scouring and de-agglomeration for immediate use by the user without the problem of cake buildup.

The cartridge is preferably large enough to be easily handled by persons of all ages, whether or not they suffer from debilitating arthritis. Once the cartridge is placed in the device, it may be merely rotated to bring the next dose into position for injection into the aerosolizing chamber. Because there is no longer the piercing of a capsule or use of vacuum or centrifugal force to remove the medicine from the capsule, users need no longer strain to suck the medicine into their lungs.

In a preferred embodiment aerosolizing chamber of this invention is mounted transverse to the major air flow passing through the device and has an electric motor driven impeller disposed therein but in nonconcentric alignment therewith, with one edge of the impeller lying very close to one edge of the chamber. A plurality of paddle wheels mounted about the periphery of the impeller cause extreme unbalanced turbulence when the impeller is rotated at high speed thereby causing the powdered medicine to undergo a self-scouring operation within the chamber to insure that all the medicine is thereafter carried into the airstream to be swept into the user's lungs. This turbulence causes the particles to collide repeatedly and at a high-energy level. Such interaction causes comminution of the medicine to reduce the large agglomerated particles to their original size which can be more efficiently inhaled into the lungs. It also reduces the problem of cake buildup to negligible proportions.

The airstream preferably drawn through the device by the user when inhaling the medicine is throttled to limit the exit velocity of the aerosol to lower the incidence of particle loss to the moist tissue in the user's throat. When the user stops to take a breath or to exhale between inhalations, the impeller stops spinning and the air flow from the device immediately ceases. This prevents loss of medicine from the aerosolizing chamber. Upon subsequent inhalation, the medication remaining in the chamber is again aerosolized for passage into the airstream. In this manner, the full dosage is provided for inhalation in one or more breaths. Thus, the user is spared the uncomfortable aspect of prolonged repeated inhalations such as found in a liquid nebulizer. A portion of the air stream is introduced into the aerosolizing chamber to sweep the particles from the chamber and to produce a low-density aerosol mist of fine medication powder that may be easily and safely inhaled deep into the lungs to maximize the effects of the medicine.

Accordingly, it is an object of this invention to provide apparatus for aerosolizing repeated doses of dry medication powders wherein the doses may be carried within a cartridge that is itself carryable in the device to eliminate the need for having multiple capsules of medicine on one's person. Other objects include a device utilizing a specific cartridge that contains a plurality of individual doses of powdered medication for successive inhalation therapy without the need to load and unload separate gelatin capsules; a device that permits full introduction of the medicine dose into the aerosolizing chamber in one, short mechanical movement to eliminate the need for relying on centrifugal force or vacuum to slowly extract the medicine through the perforated walls of a gelatin capsule; a device whose aerosolizing energy comes from a motor-driven impeller and not the user's breath, so that the efficiency of aerosolization is independent of user-efforts; a device that utilizes an impeller non-concentrically mounted in the aerosolizing chamber to produce unbalanced turbulence therein and reduce the incidence of medicine cake buildup within the chamber; a device that limits the exit velocity of the aerosol from the chamber; a device that prevents exhalation of moisture-laden breath therein to remove the opportunity for the medicine powder to become moistened and cake within the aerosolizing chamber or some other portion of the unit; a device that causes throttling of the intake airstream through the unit to prevent medicine particles from reaching a high velocity and become attached to the soft, moist tissues surrounding the throat of the user that normally prevents utilization of the medicine deep within the lungs; and, a device that will only begin to administer the medicine during normal inhalation of the airstream and medicine by the user. Still other objects of the invention include a process of preparing the medicine to be made totally available for inhalation into the lungs of the user and a method of treating powdered medicine to insure full aerosolization of the dose. These and other objects of the invention will become more apparent when reading the description of the preferred embodiment that follows, taken together with the drawings that are appended hereto. The scope of protection sought by the inventors may be gleaned from a fair reading of the claims that conclude this specification.

DESCRIPTION OF THE DRAWINGS

FIG. 1 is a top plan view of the preferred embodiment of the apparatus of this invention;

FIG. 2 is a side elevational view of the embodiment shown in FIG. 1 with the dosage injector handle lifted out of its secured, traveling position and the front piece rotated downward to expose the interior of the device;

FIG. 3 is a top sectional view of the preferred embodiment taken along lines 3—3 in FIG. 2;

FIG. 4 is a front sectional view taken along lines 4—4 in FIG. 3 showing the aerosolizing chamber and the impeller in nonconcentric relationship;

FIG. 5 is another front sectional view taken along lines 5—5 in FIG. 3 forward of the rear wall of the front mouth piece showing the preferred position of the air inlet holes;

FIG. 6 is a front end view of the embodiment shown in FIG. 1;

FIG. 7 is a rear end view of the embodiment shown in FIG. 1;

FIG. 8 is a closeup view of the aerosolizing chamber showing the position of the impeller in non-concentric relationship therein;

FIG. 9 is a side elevational sectional view of the impeller shown in FIG. 8;

FIG. 10 is a top plan view of the assembled dose cartridge usable in the embodiment shown in FIG. 1;

FIG. 11 is a sectional side view of the dose cartridge taken along lines 11—11 in FIG. 10;

FIG. 12 is a top view of the ring portion of the cartridge showing the apertures for holding the doses of medicine; and, FIG. 13 is a top view of one of the cover plates shown in FIG. 10.

DESCRIPTION OF THE PREFERRED EMBODIMENT

As shown in the drawings wherein like elements are identified by like numerals throughout the 13 figures, FIGS. 1-3 show the overall view of the preferred embodiment wherein an inner core or housing 1 preferably made of plastic or other lightweight material, including a hollow front end piece 3, pivotally mounted thereto by a pair of tabs 5 extending therefrom through which pass a pair of pins 7 whose ends are mounted in core 1 for pivoting piece 3 outward and downward from core 1, said front end piece further including a centralized hollow tubular mouth or nose piece 9 formed at the front thereof and a rear closure wall 11 transversely closing over the rear of piece 3. A back end piece 13 is attached to said core 1 about a marginal edge 15 by a snap skirt 17 or other known connection means. Core 1 conveniently has a flattened bottom 19, a pair of spaced apart rounded sidewalls 21a and 21b and a flattened disk receipt surface 23 for easy grasp by the user.

As shown in FIGS. 2, 3, 4 and 8, a disk-shaped or circularly-shaped aerosolizing chamber 25 is formed in the front wall 27 of core 1 and arranged vertical to core bottom 19 or transversely to the air flow, shown by the arrows in FIGS. 2 and 3 exiting mouthpiece 9. Chamber 25 is small, preferably on the order of one-half inch in diameter and one-eighth inch thick and is bounded at the front by a portion of front piece rear closure wall 11, at the back by a smooth wall 29 and about the periphery by a circumferential wall 30.

An impeller 31, shown in FIGS. 3, 4, 8 and 9 to comprise a thin, flat circular plate 33, defined by a peripheral marginal edge 35, having mounted thereabout a plurality of short paddle blades 37 arranged normal to the plane of plate 33 and preferably fixed to peripheral edge 35, is disposed in chamber 25 in non-concentric relationship therewith and more particularly positioned below the geometric center of aerosolizing chamber 25 toward the lower part of circumferential wall 30. Impeller 31 is mounted on a central shaft 39 that extends through an aperture 41 formed in rear chamber wall 29 and arranged for high-speed power rotation about a fixed axis small x—x. Shaft 39 is connected to a high-speed electric motor 43 that is driven by at least one, but preferably a pair of electric batteries 45 carried in space-apart bores 47a and 47b formed in core 1. When front end piece 3 is moved out of assembly with core 1, by pivoting it about pins 7 as shown in FIG. 2, aerosolizing chamber 25 is opened and exposed for maintenance or cleaning.

As shown in FIGS. 3, 5 and 7 the present device includes an air flow path 49 which passes a first throttled stream of air through inner core 1 toward mouthpiece 9 for inhalation by the user. At least one aperture 51 formed in back end piece 13 for receiving outside air into core 1. Passage ways 53 are formed through inner core 1, in communication with aperture 51, to allow passage of said airstream, shown by arrows in FIGS. 2 and 3, through core 1 toward mouthpiece 9, said passage ways exiting into hollow front end piece 3 through at least one but preferably a plurality of throttling apertures or openings 55 formed in front end piece rear closure wall 11 as shown in FIG. 5. The size of aperture 51, passage ways 53, and apertures 55 are set to provide significant resistance to air flow thus throttling the velocity of said airstream through core 1 and into the user's mouth to reduce particulate momentum and hence impaction against the rear of the user's throat.

A portion of the first stream of air is diverted into a second stream of air, as shown by the arrows in FIGS. 2 and 3, for sweeping through aerosolizing chamber 25 and carrying the powdered medicine into the first stream of air for inhalation through mouthpiece 9 by the user. This is accomplished by providing a first inlet aperture or opening 59 formed in front end piece rear closure wall 11 near the center of impeller 31. A second chamber outlet aperture or opening 61 is formed in front end piece rear closure wall 11 at the top of aerosolizing chamber 25. As motor 43 drives impeller 31 at a high speed, the impeller acts as a centrifugal air pump drawing air in through first inlet aperture 59, mixing said air with the full dose of powdered medicine inside chamber 25 and expelling the air and medicine as a fine, low-density dry mist out through chamber outlet aperture 61 for combining with the first throttled stream of air into mouthpiece 9 for inhalation by the user. Apertures 59 and 61 are sized such that the aerosol emerges from chamber 25 through aperture 61 at a clinically negligible velocity. The size of inlet aperture 59 may be set, for example, at 0.093 inches in diameter and the size of outlet aperture 61 may be set, for example, at 0.062 inches in diameter. This low velocity combines with the first throttled airstream to produce a fine, lowdensity dry mist that is easily inhaled by the user without forced inhalation.

Impeller 31 is rotated by electric motor 43 at extremely high speed such as 12,500 rpm. Such a high speed causes a high velocity flow and turbulence of the powder in the aerosolizing chamber and, with the unbalancing of this flow, caused by the offset of impeller 31, causes the particles to impact each other and chamber walls 11, 29 and 30 to comminute and disaggregate them into smaller, more easily respirable-size particles and further causes them to become intimately mixed with the air flow passing therethrough to provide a self-cleaning action on the walls of the chamber. Because of the offset location of impeller 31 in chamber 25, the high velocity circulation of air is at a different pressures and velocities at different points about chamber 25 that promotes turbulent mixing of the particles and air and eliminating the problem of caking of the powdered medicine. As shown in FIG. 5, inlet aperture 59 can be place over a wide area below impeller boss 62 but it is preferred to locate it just below boss 62 and above paddles 37 to provide a less restricted entrance into chamber 25. Similarly, outlet aperture 61 may be located virtually anywhere above impeller boss 62 but it is preferred to locate it above paddles 37 and on one side or the other of the centerline of chamber 25. Should the user attempt to draw or suck air in through mouthpiece 9 at a high rate, a partial vacuum will be created in inner core 1, however this vacuum would exist over the total internal volume of inner core 1 so that the centrifugal pumping action of offset impeller 31 would be unaffected by the vacuum or by the degree to which the user draws or sucks on mouthpiece 5.

A multi-dosage medicine containing cartridge 63 is shown in FIGS. 10-12 for use in this device. As shown in FIG. 12, cartridge 63 comprises a relatively thin ring 65 of plastic or other lightweight material having a scalloped outer marginal edge 67 and a smooth inner edge 69. A series of apertures 71 are formed transverse to the plane of and through ring 65 between outer edge 67 and inner edge 69 and adapted for receipt of doses of powdered medicine therein. A pair of cover plates 73a and 73b having a thin outer portion 75 bounded by an outer marginal edge 77 and a thicker inner portion 79 are provided to cover both sides of ring 65 as shown in FIGS. 10 and 11. A U-shaped opening 81 is formed in the thin outer portion 75 of each cover plate and the plates placed in faced-together arrangement, as shown in FIG. 11, to sandwich ring 65 therebetween. Cover plate outer marginal edge 77 is sized to terminate short of ring scalloped outer edge 67 as shown in FIG. 10. U-shaped openings 81 in cover plates 73a and 73b are aligned one above the other as shown in FIG. 10 so that the particular dose of medicine contained in said apertures are exposed, one at time, as ring 65 is rotated between cover plate 73a and 73b. A center depression 83 is formed in cover plates 73a and 73b adjacent a center bore 85 formed there through and a hollow rivet 87 or other fastening device is placed in said bore and folded over at each end to hold cover plates 73a and 73b in fixed covering arrangement over ring 65.

A medicine dosage supplier 89 is provided for mounting dosage cartridge 63 in operable communication with inner core 1 and provides instantaneous introduction of the medicine into aerosolizing chamber 25. The dosage supplier 89 is shown in FIGS. 1 and 2 to include a hold-down lever 91 pivoted by a pin 93 mounted in back end piece 13. An open area 95 is formed in core top surface 23 for receipt of dosage cartridge 63 on a center peg 97. An offset peg 98 is also provided to extend into a small aperture 99 formed through plates 73a and 73b to immobilize cover plates 73a and 73b. A fastening post 100 containing a spring loaded ball catch 101 depends from the front end of hold down lever 91 and is adapted for insertion into a receiving bore 103 formed in the upper rear portion of front end piece 3.

A medicine-charging plunger 105, with a T-shaped top bar 106, is reciprocally mounted in a bore 107 in hold-down lever 91 and biased upward by a spring 109 against a stop 110 formed in plunger 105. A medicine-charging passage way or chute 111 is formed in inner core 1 below plunger 105 down into the top of aerosolizing chamber 25. It is preferred to set the size of chute 111 at the diameter of aperture 71. In use, dosage cartridge 63 is placed on pegs 97 and 98 in open area 95 and hold-down lever 91 is pivoted downward there-over to retain said cartridge and lock mouthpiece 9 in its operable closed position. U-shaped openings 81 in cover plate 73a and 73b are automatically aligned below medicine-charging plunger 105 by the arrangement of aperture 99 and offset peg 98. Aerosolizing chamber outlet 61 is preferably offset from just below chute 111 to prevent interference with the charging of medicine or with having outlet 61 becoming jammed with medicine during charging. A spring-loaded ball 113, shown in FIG. 1, is formed in rear end piece 13 so that said ball is biased against ring scalloped outer edge 67 to prevent unwanted movement of dosage cartridge ring 65. Ring 65 is then rotated to bring a medicine filled aperture 71 into alignment over medicine-charging passage way 111 and charging plunger 105 is pressed downward against the bias from spring 109 to pass the full dose of powdered medicine directly and instantaneously into aerosolizing chamber 25. Thereafter, plunger 105 will remain in medicine-charging passage way 111 to form the top portion of circumferential wall 30 of aerosolizing chamber 25 and may be held there, against spring bias by rotating plunger handle 106 under overlying leaves 117 that are spaced about a hollow area 119 formed in the front part of hold down lever 91 as shown in FIG. 1.

A one-way valve assembly 121 is provided for preventing exhalation by the user into the apparatus so that no moisture is available to cake the medicine. The valve assembly 121 includes a one-way valve or flapper hingedly mounted by pin 125 interior of aperture 51 in back end piece 13. A spring 127 is connected to flapper 123 to biased it into closed relationship with aperture 51 during all handling of the apparatus other than when the user is drawing air in through mouthpiece 9. When the user inhales or draws air in through inner core 1, the reduction of internal pressure in core 1 allows atmospheric pressure on flapper 123 to overcome the bias of spring 127 and force it to open to admit air into inner core 1 to create the first stream of air as previously described. A normally-opened electric switch 129 is connected to flapper 123 and interconnected between electric motor 43 and batteries 45 through an electric box 131, formed in core 1, to insure that motor 43 is not energized by batteries 45 unless flapper 123 is opened. Flapper 123 will open when the user draws air in through mouthpiece 9 to inhale the aerosolized powdered medicine.

It is recognized in the prior art that powder medication having a particle size on the order of 1 to 20 microns tends to build up in the aerosolizing chamber. This invention has reduced the problem associated with high humidity. Desiccant packages, used in prior art devices are not required. However, various amounts of humidity occurring at the time the powders are subdivided into dosage form may provide an environment conducive to a certain amount of initial caking. Accordingly, notwithstanding the virtues of this invention, some caking still may occur due to matters beyond the control of the user.

Further, the volume of many medicines, in their dosage amounts, is often extremely small. It has been a practice for many years to dilute these small volumes with inert filler materials to increase the overall volume to handleable sizes, such as is seen in aspirin tablets and the like. So too, in the field of inhalable powder medicines has there been an established practice of adding inert powders to the medicine to bring the volume up to a size that can be efficiently inhaled.

It appears that little or no attention has been paid to the size of particles of inert powder vis-a-vis the problem with large particle momentum and cake buildup. We have discovered that mixing a quantity of carefully sized, substantially larger particle inert powder with virtually any dosage of finely powdered medicine will provide a useful mixture of particle sizes for the dose that will intermix or undergo comminution and self-scouring in the aerosolizing chamber of this apparatus to cause the medicine powder to be disaggregated and comminuted into small sized particles able to be swept out of the aerosolizing chamber first, while the larger particles of inert material act to scour and clean the internal surfaces of the aerosolizing chamber and thereafter undergo self-comminution and self-scouring for inhalation by the user. Because of the low velocity of air coming through the mouthpiece by virtue of the throttling action of first means 49, there is insufficient momentum given to any large particles to cause impaction with the soft moist tissue of the throat and larynx. Accordingly, by providing a diluent in the form of particles of nontoxic substances, such as lactose, where a substantial amount of them are in the size range of 50 micron diameter particles and higher, the small particle powdered medicine is insured of being cleared out of the aerosolizing chamber notwithstanding the initial humidity that may accompany the medicine from the dose cartridge into the chamber.

Electrical wiring in these drawings has not been shown for clarity; such wiring is already known in the prior art. While the invention has been described with reference to a particular embodiment hereof, those skilled in the art will be able to make various modifications to the described embodiment of the invention without departing from the true spirit and scope thereof. It is intended that all combinations of elements and steps which perform substantially the same function in substantially the same way to achieve the same results are within the scope of this invention.

What is claimed is:

1. A device for aerosolizing powdered medicine comprising:
    a housing;
    a generally planar front chamber wall, a generally planar back chamber wall, and a chamber circumferential wall, within the housing, forming a generally disk-shaped aerosolizing chamber;
    an impeller positioned within the aerosolizing chamber and rotatable therein about an impeller axis, in a plane parallel tot he front and back chamber walls, with the front chamber wall spaced apart from the back chamber wall by less than one diameter of the impeller;
    a motor linked to the impeller to spin the impeller within the aerosolizing chamber; and
    at least one inlet opening and at least one outlet opening respectively extending generally parallel to the impeller axis, into and out of the aerosolizing chamber.

2. The device of claim 1 further comprising a mouthpiece hingedly attached to the housing, the mouthpiece including the front chamber wall and pivotable from a closed position wherein the front chamber wall engages the chamber circumferential wall to enclose the aerosolizing chamber, to an open position wherein the front chamber wall is apart from the chamber circumferential wall, to allow for cleaning of the aerosolizing chamber.

3. The device of claim 1 wherein the outlet opening is adjacent the chamber circumferential wall.

4. The device of claim 1 wherein the impeller has a diameter approximately four times larger than the spacing between the front and back chamber walls.

5. The device of claim 1 further comprising a multidose medicine-carrying cartridge rotatably attachable tot he housing, the cartridge including a central ring having a plurality of apertures for holding a powdered drug, a top plate and a bottom plate attached to each other on either side of the central ring, with the central ring slidably rotatable between the top and bottom plates.

6. The device of claim 5 further comprising means for delivering a dose of medicine from the cartridge into the aerosolizing chamber.

7. The device of claim 6 wherein the housing comprises a generally flat bottom surface and a generally flat cartridge receiving surface.

8. The device of claim 1 wherein the impeller is rotatable about an impeller axis positioned below a chamber axis parallel to the impeller axis and passing through the center of the aerosolizing chamber.

9. The device of claim 1 wherein the motor is located outside of the aerosolizing chamber.

10. A device for delivering inhaled powders comprising:
    a housing including a disk-shaped aerosolizing chamber formed by spaced apart flat front and rear walls on either side of a circumferential wall;
    a hollow nose/mouthpiece attachable to the housing;
    a motor having a shaft, contained within the housing;
    an impeller mounted on the motor shaft and eccentrically positioned within the aerosolizing chamber;
    means for introducing a powder into the aerosolizing chamber;
    means for receiving a first stream of air into the housing and directing it towards the mouthpiece; and
    means for diverting a portion of the first stream to form a second stream of air for flowing from the mouthpiece through the aerosolizing chamber and back into the mouthpiece.

11. The device of claim 10 further comprising a pivot attachment for attaching the mouthpiece to the housing.

12. The device of claim 10 wherein the mouthpiece comprises the front wall of the aerosolizing chamber.

13. The device of claim 10 wherein the means for diverting comprises an entry opening through the front wall of the aerosolizing chamber adjacent to the center of the impeller and an exit opening through the front wall of the aerosolizing chamber adjacent the circumferential wall.

14. The device of claim 10 further comprising a multidose cartridge including a ring having a multiplicity of powder filled apertures.

15. The device of claim 14 further comprising a charging passageway extending through the housing from the aerosolizing chamber to the ring.

16. The device of claim 10 further comprising a flapper valve to prevent exhalation into the device, and a switch linked to the flapper valve and motor.

17. The device of claim 10 wherein the means for receiving comprises a plurality of throttling openings leading from the interior of the housing into the mouthpiece.

18. A device for aerosolizing powdered medicine comprising:
    a housing;
    a generally planar front chamber wall, a generally planar back chamber wall, and a chamber circumferential wall, within the housing, forming a generally disk-shaped aerosolizing chamber;
    an impeller positioned within the aerosolizing chamber and rotatable therein about an impeller axis in a plane parallel to the front and back chamber walls, with the front chamber wall spaced apart from the back chamber wall by less than one diameter of the impeller;

drive means for spinning the impeller within the aerosolizing chamber;

at least one inlet opening and at least one outlet opening respectively extending into and out of the aerosolizing chamber generally parallel to impeller axis;

an outside air opening adjacent the back end of the housing, opposite the mouthpiece;

a passageway within the housing connecting to the outside air opening; and at least one throttling opening bypassing the aerosolizing chamber connecting to the passageway and leading into the mouthpiece.

19. The device of claim 1 wherein the impeller is eccentrically positioned within the aerosolizing chamber.

20. A device for aerosolizing powdered medicine comprising:

a housing;

a generally planar front chamber wall, a generally planar back chamber wall, and a chamber circumferential wall, within the housing, forming a generally disk-shaped aerosolizing chamber;

an impeller positioned within the aerosolizing chamber and rotatable therein in a plane parallel to the front and back chamber walls;

a motor linked to the impeller to spin the impeller within the aerosolizing chamber;

at least one inlet opening and at least one outlet opening extending into the aerosolizing chamber;

a flap valve on the housing for preventing exhalation into the device; and a switch linked to the flap valve and motor to turn the motor on when the valve opens.

21. A dry powder inhaler comprising:

a housing;

a front chamber wall, a back chamber wall, and a chamber circumferential wall, within the housing, forming a generally disk-shaped aerosolizing chamber;

an impeller positioned within the aerosolizing chamber and rotatable therein about an impeller axis in a plane parallel to the front and back chamber walls with the front chamber wall spaced apart from the back chamber wall by less than one diameter of the impeller;

a motor linked to the impeller to spin the impeller within the aerosolizing chamber; and at least one inlet opening and at least one outlet opening extending generally parallel to the impeller axis, into and out of the aerosolizing chamber;

a cartridge containing a plurality of powdered drug dose, the cartridge supported on the housing; and a chute passing through the housing and leading from the cartridge to a chute opening generally aligned with the impeller into the aerosolizing chamber, such that powdered drug passing through the chute is deposited, at least in part, on the impeller.

22. The device of claim 21 wherein the impeller has a plurality of equally spaced apart flat radial paddles.

* * * * *